US008623420B2

(12) United States Patent
Costa et al.

(10) Patent No.: US 8,623,420 B2
(45) Date of Patent: Jan. 7, 2014

(54) SWEET WHEY BASED BIOPESTICIDE COMPOSITION

(75) Inventors: Scott D. Costa, Waterville, VT (US); Stacie Grassano, Morrisville, VT (US); Jiancai Li, Littleton, CO (US)

(73) Assignee: University of Vermont and State Agriculture College, Burlington, VT (US)

( * ) Notice: Subject to any disclaimer, the term of this patent is extended or adjusted under 35 U.S.C. 154(b) by 536 days.

(21) Appl. No.: 12/518,114

(22) PCT Filed: Dec. 7, 2007

(86) PCT No.: PCT/US2007/086838
§ 371 (c)(1),
(2), (4) Date: Aug. 16, 2010

(87) PCT Pub. No.: WO2008/073843
PCT Pub. Date: Jun. 19, 2008

(65) Prior Publication Data

US 2010/0303764 A1 Dec. 2, 2010

Related U.S. Application Data

(60) Provisional application No. 60/869,227, filed on Dec. 8, 2006.

(51) Int. Cl.
*A61K 35/20* (2006.01)
*A01N 25/00* (2006.01)
*A01N 63/04* (2006.01)

(52) U.S. Cl.
USPC ........... 424/535; 424/405; 424/520; 424/93.5

(58) Field of Classification Search
USPC ................. 424/400, 405, 407, 93.5, 520, 535
See application file for complete search history.

(56) References Cited

U.S. PATENT DOCUMENTS

| | | | | |
|---|---|---|---|---|
| 3,087,865 | A | 4/1963 | Drake et al. | |
| 4,530,834 | A | 7/1985 | McCabe et al. | |
| 5,246,842 | A * | 9/1993 | O'Brien et al. | 435/134 |
| 5,360,607 | A | 11/1994 | Eyal et al. | |
| 5,413,784 | A | 5/1995 | Wright et al. | |
| 5,811,095 | A | 9/1998 | Williamson et al. | |
| 5,989,543 | A | 11/1999 | Davide et al. | |
| 6,254,864 | B1 | 7/2001 | Stimac et al. | |
| 6,524,601 | B1 | 2/2003 | Shapiro et al. | |
| 6,660,290 | B1 | 12/2003 | Stamets | |
| 6,942,860 | B2 | 9/2005 | Warrior et al. | |
| 7,045,138 | B2 | 5/2006 | Kennedy et al. | |
| 7,122,176 | B2 | 10/2006 | Stamets | |
| 7,241,612 | B2 | 7/2007 | Shapiro-Ilan et al. | |
| 2005/0191287 | A1 | 9/2005 | Gomes Sanches et al. | |
| 2007/0148203 | A1 | 6/2007 | Parker et al. | |

FOREIGN PATENT DOCUMENTS

| | | |
|---|---|---|
| EP | 570089 | 11/1993 |
| EP | 1570048 | 9/2007 |
| WO | WO9211856 | 7/1992 |
| WO | WO9525430 | 9/1995 |
| WO | WO9535365 | 12/1995 |
| WO | WO2004052103 | 6/2004 |
| WO | WO2005009360 | 2/2005 |

OTHER PUBLICATIONS

J.E. Curtis, T.V. Price and P.M. Ridland, "Initial Development of a Spray Formulation Which Promotes Germination and Growth of the Fungal Entomopathogen *Verticillium Iecanii* (Zimmerman) Viegas (Deuteromycotina: Hyphomycetes) on Capsicum Leaves (*Capsicum annum grossum* Sendt. var. California Wonder) and Infection of *Myzus persicae* Sulzer (Homoptera: Aphididae)"; Biocontrol Science and Technology (2003) 13, pp. 35-46.

Scott D. Costa, Bruce L. Parker, Vladimir Gouli, Michael Brownbridge, Margaret Skinner, and Svetlana Gouli; "Insect-Killing Fungi as a Component of Hemlock Woolly Adelgig Integrated Pest Management," Third Symposium on Hemlock Wooly Adelgid; pp. 155-159.

Written Opinion of the International Searching Authority in International Application No. PCT/US2007/086838.

* cited by examiner

*Primary Examiner* — Ruth Davis
(74) *Attorney, Agent, or Firm* — Downs Rachlin Martin PLLC

(57) ABSTRACT

A biopesticide composition for pest management that includes a sweet whey product and spores mixed with a carrier to form a growing environment in a target region. The growing environment forms a micro-factory that is suitable for spore growth, such that the number of spores substantially increases from a first spore concentration prior to application to the target region to a second spore concentration after a period of time. The biopesticide composition may include other additives that modify the micro-factory in a manner that facilitates spore growth and/or increases the probability that a target pest, e.g., an insect, will come into contact with the spores.

22 Claims, 3 Drawing Sheets

SWEET WHEY BASED BIOPESTICIDE COMPOSITION

RELATED APPLICATION DATA

This application claims the benefit of priority of U.S. Provisional Patent Application Ser. No. 60/869,227, filed Dec. 8, 2006, and titled Whey-Based Fungal Micro-Factory, which is incorporated by reference herein in its entirety.

FIELD OF THE INVENTION

The present invention generally relates to the field of biopesticides. In particular, the present invention is directed to a sweet whey-based biopesticide composition.

BACKGROUND

Many species of plants, plant pathogens, insects, and animals are considered pests in that they reduce agricultural productivity, diminish aesthetics and economic value of ornamental plants and threaten the health of natural resources such as forest, rangeland and aquatic environments. For instance, invasive plants and plant pathogens, such as, for example, dwarf mistletoe, weedy *Rubus* spp., leafy spurge, clidemia and miconia shrubs, kudzu, Annosnum root rot, beech bark disease, and frosty pod rot, often grow unimpeded and can supplant or destroy native plant species. Similarly, insects like Asian longhorn beetles, emerald ash borers, gypsy moths, hemlock wooly adelgid, bark beetles, Douglas-fir tussock moth, western spruce budworm, pear thrips, and elongate hemlock scale, attack healthy trees, plants, and other flora in a manner that is detrimental to the well being of such trees, plants and other flora and as a consequence, detrimental to other plants and animals native to the forest environment. Diseases and other pests of, but not limited to, agricultural crops, ornamentals and turf are numerous. Pest species require management if desirable characteristics of their hosts are to be preserved.

Many approaches for managing these threats rely almost exclusively on synthetic chemical pesticides. Although such pesticides may be effective at controlling undesirable organisms, increased awareness about the adverse effects of these chemical compositions on water quality, non-targeted species, and humans provides motivation to introduce safer alternatives. Among alternatives being studied, biologically-based compositions that use fungi ("biopesticides") are showing significant promise when used to control populations of certain targeted pests. These biopesticides are effective because they produce spores, conidia, mycelium, and other fungal units (hereinafter collectively, "spores") that infect healthy targeted pests in a manner that causes disease and, eventually, death.

Despite the desirable pathogenic effects that these biopesticides display, inadequate and cost effective production and delivery approaches are limiting their widespread adoption. Spore production, for instance, is often accomplished in limited batches or in facilities that require substantial capital investment to produce quantities of spores suitable for a biopesticide application. Balanced against these high production costs are the health and safety benefits, reduced ecological impact, and value added potential, e.g., organic labeling, derived by pest management and forest preservation that use biopesticides instead of chemicals. Unfortunately, without significant reduction in the fixed costs associated with spore production, this balance often tips in favor of the known chemical pesticides.

The efficacy of a biopesticide is often limited by physical constraints associated with its formulation, such as, for example, relatively high viscosity of low volume applications containing sufficient spores ($1\times10^{13}$ spores/acre) that does not meet the requirements for effective aerial applications. Because many biopesticides cannot be effectively applied to a target region, e.g., a forest, they are unable to provide the required number and concentration of spores for effective pest management. Without providing the proper concentration of the spores after delivery, the biopesticidal composition will not be an effective substitute for the chemical pesticides described above.

Known pest management practices involving the use of biopesticide compositions typically have a high concentration of spores to achieve effective mortality of the targeted pests. Such concentrations are often in excess of $1\times10^{8}$ spores/ml (of the biopesticide composition) when 200 liter/acre are applied, and concentration increases as delivery volume is reduced. Such practices that use high numbers of spores are often not economically viable because of the relatively high cost of producing the number of spores required to meet the desired rates of pest mortality. Accordingly, farm managers, agriculturists, foresters and others seeking to implement biological control agents as part of their management regimes would welcome a biopesticide solution that can increase the concentration of the spores after delivery so as to improve the efficacy and economics of the biopesticide technique.

SUMMARY OF THE DISCLOSURE

In one implementations, a biopesticide composition, comprising a plurality of fungal spores; and a sweet whey product nutritive to the plurality of fungal spores, the sweet whey product having a first percentage of lactose of at least about 2% by weight percentage of said sweet whey product.

In another implementation, a biopesticide composition applicable to a target region having a plurality of targeted pests, the biopesticide composition comprising a fungal material including a plurality of spores selected so as to cause mortality of the plurality of targeted pests; and a sweet whey product nutritive to the plurality of spores and forming at least about 2% by weight percentage of the biopesticide composition, the sweet whey product having a first percentage of lactose of at least about 2% by weight percentage of the sweet whey product.

In yet another implementation, a method of managing targeted pests in a target region, the method comprising providing a biopesticide composition that includes a plurality of fungal spores having a first concentration and a sweet whey product nutritive to the plurality of fungal spores, wherein the sweet whey product has a second concentration, the first and second concentrations being selected so that the first concentration will increase at least ten (10) times within one week when incubated under selected conditions; applying the biopesticide composition to a target region; and incubating the biopesticide composition in the target region at a temperature from about 10° C. to about 30° C. and a relative humidity from about 70% to about 95% so as to cause the first concentration of fungal spores to increase at least ten (10) times after about fourteen (14) days.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
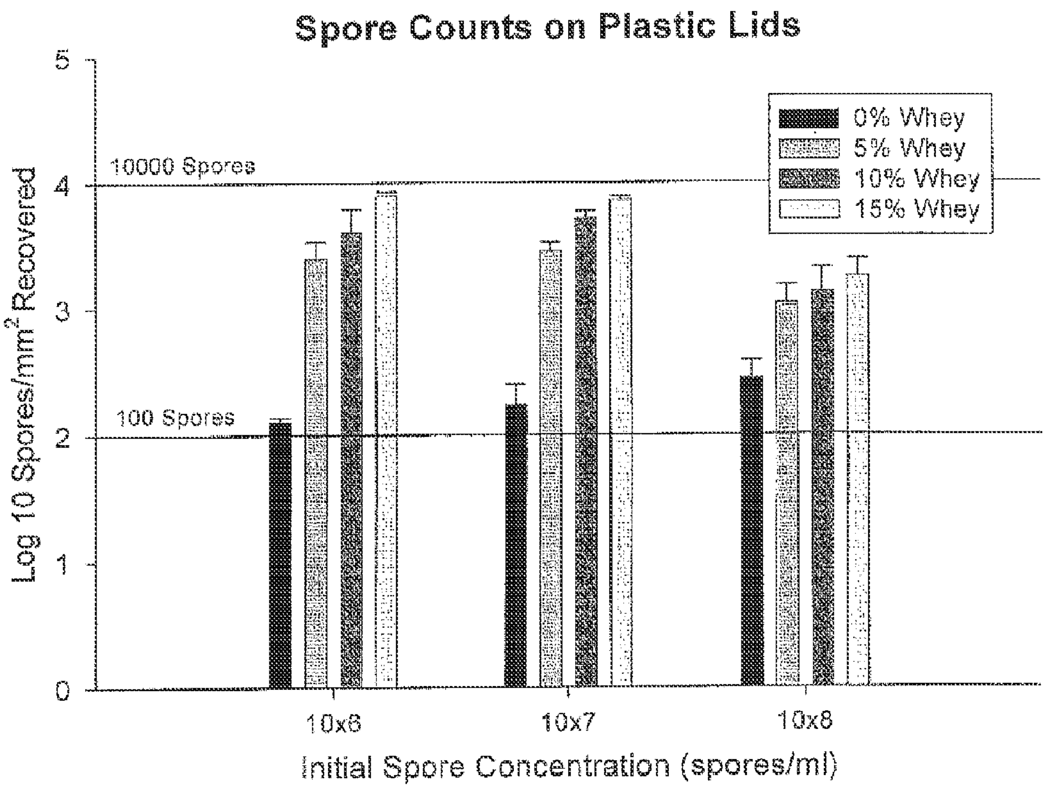
FIG. 1 is a graph that compares the final spore concentration for micro-factories formed from several biopesticide compositions.

Biopesticide compositions in accordance with concepts of the present invention may provide a substantially cost-competitive replacement for the chemical pesticides discussed in the Background section above. Such biopesticide compositions include a nutrient source that sustains the reproductive activities commonly associated with spores that cause mortality or suppression among the insects, plants, plant pathogens and other targeted pests of the type discussed in the Background section above. These spores may come from mycopathogenic, suppressive, and/or antagonistic fungi. As discussed more below, when applied to a target region, e.g., a forest, implementations of the present biopesticide composition may facilitate spore growth during typical fluctuations in environmental conditions, e.g., temperature, humidity, and ambient sunlight, so as to increase the concentration of spores over time, and increase the probability of mortality among the targeted pests.

A biopesticide composition in accordance with concepts of the present invention includes a nutrient source from a whey by-product formed during the production of dairy goods. More particularly, an example of a suitable whey by-product is a sweet whey product that includes lactose and lactic acid components. These components may result from dairy production procedures in which there is insignificant conversion of lactose to lactic acid. Other sweet whey products, for instance, may be obtained from cheese manufacturing procedures that utilize an enzyme, e.g., rennet, chymosin, and/or rennin. Yet other sweet whey products may be obtained from cheese manufacturing procedures that produce rennet-type hard cheeses, e.g., cheddar, Swiss or mozzarella cheeses. Sweet whey may also be obtained from other manufacturing procedures known by those ordinarily skilled in the art.

Implementations of the biopesticide composition may also include liquid sweet whey product or a dry sweet whey product. Sweet whey liquid is a form of a sweet whey product that has a greater moisture content by weight percentage than its corresponding solid content. An example of liquid sweet whey product includes about 6.35% total solid and about 93.65% moisture (by weight percentage). Sweet whey powder (or dry sweet whey), on the other hand, is a dried form of a sweet whey product with a powder-like consistency known in the art. This form has a greater solid content by weight percentage than its corresponding moisture content. An example of a sweet whey powder includes about 96.5% total solid and about 3.5% moisture (by weight percentage).

In addition to lactose and lactic acid, a sweet whey product usable with the present biopesticide composition may also include other components. These components include protein, ash, and fat, among others. As discussed in more detail below, the composition of the sweet whey product can be expressed in terms of individual percentage of these components (as well as lactose and lactic acid) as a function of the total weight. In general, sweet whey product in dry form has a percentage of lactose that is greater than the percentages of each other constituent component. In one example, the dry sweet whey product includes about 75% lactose, about 13.10% protein, about 7.3% ash, about 0.8% fat, and about 0.2% lactic acid (by weight percentage). In another example, the liquid sweet whey product includes about 4.85% lactose, about 0.8% protein, about 0.5% fat, about 0.5% ash, and about 0.05% lactic acid (by weight percentage). Additional examples that include ranges for these components will be discussed in connection with Table 1 below, which provides ranges for the components of the sweet whey product and percentage of moisture, (each by their respective weight percentage).

TABLE 1

| Sweet Whey Composition | | | | |
|---|---|---|---|---|
| | Sweet Whey Powder | | Sweet Whey Liquid | |
| | Min | Max | Min | Max |
| Lactose | 64% | 78% | 2% | 7% |
| Protein | 11% | 14% | 0.4% | 2% |
| Ash | 6% | 8% | 0.3% | 1% |
| Fat | 0.6% | 1% | 0.3% | 1% |
| Lactic Acid | 0.04% | 0.1% | 0.1% | 0.3% |
| Moisture | 3% | 6% | 85% | 97% |
| Solid | 97% | 94% | 15% | 3% |

An alternative way to characterize sweet whey product used in the biopesticide composition relies on certain properties of the sweet whey product known in the art. Titratable acidity value, for instance, expresses the percent of lactic acid on a reconstituted basis of a sweet whey product. One example of a suitable sweet whey product has a titratable acidity of less than about 0.16 on a reconstituted basis. In other examples, a sweet whey product suitable for the biopesticide composition, may have a titratable acidity from about 0.08 to about 0.32.

In general, the amount of sweet whey product used in the biopesticide composition is measured according to its weight percentage, or by the mass of sweet whey in the biopesticide composition as a function of the mass of the entire biopesticide composition. This method of determining the relative composition of a biopesticide composition applies to both solid and liquid sweet whey products, as described above. It is contemplated that the weight percentage of sweet whey product will be selected based on one or more of the properties of a sweet whey product described above, or in accordance with the type and/or biological characteristics of the spores, as discussed in more detail below.

pH value is another property that can be used to characterize the sweet whey product. pH measures the total acidity of the sweet whey product. Certain implementations of the biopesticide composition include a sweet whey product with a pH value that is greater than about 5.6. It is contemplated, however, that the pH of the sweet whey product for use in the biopesticide composition may range from about 3 to about 8.

Further, alkalinity of ash is another property that describes a sweet whey product suitable for use with the biopesticide composition. In one example, a sweet whey product has an alkalinity of ash that does not exceed about 225 ml of 0.1 N HCL per 100 grams. It is contemplated, however, that other sweet whey products suitable for a biopesticide composition may have an alkalinity of ash from about 112 ml 0.1 N HCL per 100 grams to about 450 ml 0.1 N HCL per 100 grams.

The biopesticide composition also includes a carrier in which the sweet whey product is mixed to form a suspension for application into a target region, such as the forest region described above. Suitable carriers include water (e.g., distilled water, sterilized distilled water, and other types of water), oils (e.g., sunflower oil, cotton seed oil, and variations thereof), as well as other liquids having physical properties that permit the sweet whey product to be mixed in a manner that forms a suspension that can be applied into a target region.

As mentioned above, although characterized as "spores" throughout this disclosure, a biopesticide composition in accordance with concepts of the present invention may include spores, mycelium, conidia, and other fungal units that are generally associated with one or more mycopathogenic, antagonistic and suppressive fungi. Examples of such fungi include, but are not limited to, *Lecanicillium muscarium, Beauveria bassiana, Entomaphaga maimaiga*, as well as other fungi having pathogenic properties detrimental to target pests. These infectious units extract nutrition from the sweet whey product in a manner that substantially increases the preponderance of infectious units from an initial concentration at the time of deposit.

Other candidate fungi for development as biopesticides will be recognized by those ordinarily skilled in the art. Such fungi are available in research, government, private, and commercial collections, and also can be routinely isolated from the environment using techniques, processes, and other implementations recognized in the art. Suitable fungi, for instance, may be recovered from diseased target organisms by the use of standard microbiological techniques, such as applying suspensions of diseased tissue onto selective growth media to establish a culture of potential biopesticides. Other suitable fungi are also found abundantly in soil. While still other suitable fungi may be determined according to their pathogenicity and virulence. For example, it is contemplated that a fungi can be evaluated in biological activity assays where target organisms are exposed to putative pathogenic, antagonistic and suppressive fungi and the efficacy of the fungi is assessed according to one or more criteria, e.g. mortality of the target organisms.

In general, each of the various forms of fungal units (i.e., spores, conidia, mycelium) may have an initial concentration that reflects the biological structure and/or corresponding biological reproductive morphology specific to the respective infectious unit. It is contemplated that the initial concentration of fungal units in the biopesticide composition can be quantified according to methods and procedures specific to those fungal units and generally recognized in the art. When the biopesticide composition includes spores, for instance, it is contemplated that certain implementations of the biopesticide composition may include an initial spore concentration ranging from about $1\times10^4$ to about $1\times10^{10}$ spores/ml of suspension. More typically, the initial spore concentration will range from about $1\times10^5$ spores/ml of suspension to about $1\times10^7$ spores/ml of suspension in the interest of reducing the cost of the constituents of the biopesticide composition. Alternatively, when the biopesticide includes mycelium (or, a combination of spores and mycelium), the initial mycelium count may be quantified based on the amount of dry or wet biomass or as the number of colony forming units (CFUs) that arise if the mycelium is suspended in liquid and grown on a biological media.

A biopesticide composition in accordance with concepts of the present invention combines a sweet whey product, spores, and a carrier in a manner that may shift spore production away from the traditional pre-application production paradigm mentioned in the Background section above. Rather, it is contemplated that this combination will form a growing environment in the target region that is suitable for spore production so as to substantially increase the preponderance of spores from a pre-application spore concentration to a post-application spore concentration after a period of time. As described in more detail below, in addition to the sweet whey product and spores, the biopesticide composition may also include other additives in a manner and concentration that further promotes spore production and increases mortality of target insects.

Certain implementations of the biopesticide composition may include a humectant or related substance that improves hydration after the biopesticide composition is applied to a target region. It is recognized that a humectant (and similar hygroscopic materials, including those with an affinity to form hydrogen bonds with molecules of water) facilitates moisture absorption, moisture retention, and otherwise buffers moisture loss. A variety of humectants is known in the art. Examples of humectants include, but are not limited to, carrageenan, carboxylmethycellulose (CMC), gaur gum, pectin, and any combination thereof. It will be appreciated by those skilled in the art that other humectant materials are available that may fall within the scope, spirit, and concepts of the present invention such that additional examples will not be listed.

A humectant may be mixed with a carrier, a sweet whey product, and spores to form a suspension for application into a target region. Similar to the sweet whey product discussed above, the amount of a humectant used in the biopesticide composition can be measured according to its weight percentage. The weight percentage may vary according to one or more properties of the sweet whey product, spores, or characteristics of the targeted environment, among others. In general, the biopesticide composition may include in excess of about 0.001% of humectant (by weight percentage). It is contemplated, however, that typical implementations of the biopesticide composition will have from about 0.025% to about 1.5% of humectant (by weight percentage).

Certain implementations of the biopesticide composition may include one or more antimicrobials that target microorganisms and other organisms deemed competitive, predatory, or otherwise detrimental to spore growth. Such microorganisms, including bacteria, yeast, molds and undesirable fungi, may compete with spores for moisture and nutrient sources (e.g., the sweet whey product) found in the biopesticide composition. Generally, they may be encountered in the biopesticide composition before it is prepared (i.e., within the components), after it is prepared for application to the target region, and also on the target surfaces, e.g. plant foliage or soil. Examples of a suitable antimicrobial include, but are not limited to, nisin, sodium methylparaben, sorbic acid, acetic acid, and any combinations thereof. In general, the antimicrobial may be selected in accordance with attributes of the target region, or other environmental conditions identified prior to application of the biopesticide composition. In one example, the tolerance of the spores to an antimicrobial relative to the susceptibility of undesirable microorganism is considered in the selection of the antimicrobial. The number and variety of antimicrobials available for use in the biopesticide composition in accordance with concepts of the present invention will be readily appreciated by those skilled in the art.

The amount of the antimicrobial used in the biopesticide composition can also be measured according to its weight percentage as defined above. This percentage may vary according to one or more properties of the sweet whey product, spores, characteristics of the targeted environment, identified competitive microorganisms, potency of the antimicrobial and other factors. Certain implementations of the biopesticide composition will include a percentage of an antimicrobial from at least about 0.0002% of an antimicrobial (by weight percentage) to about 2% (by weight percentage). In more typical implementations, it is contemplated that the biopesticide composition will include a weight percentage of an antimicrobial from about 0.02% to about 2% (by weight percentage).

As indicated above, a biopesticide composition in accordance with concepts of the present invention may be a solid or a liquid. Regarding the former, a solid biopesticide composition may be in the form of granules, grains, micro-spheres, and other configurations. Typically, but not necessarily, the solid biopesticide composition originates as a liquid or semisolid suspension prepared by mixing spores, the sweet whey product, and one or more additives, e.g., an antimicrobial and a humectant, with a carrier solution so as to form a liquid suspension with percentages of each component as set forth above. The resultant suspension then undergoes certain processing steps consistent with preparation of one or more of the versions mentioned above. It is contemplated, for instance, that a liquid or semisolid suspension can be dried in a manner that allows spores to retain their viability using any conventional drying method, such as air drying, oven drying, freeze drying or other process recognized by those ordinarily skilled in the art. Following drying, the biopesticide composition may be processed further with known techniques until it has particles of the desired size and shape. The resultant solid biopesticide compositions may be applied en mass to a target environment using processes and techniques that will be readily appreciated by those ordinarily skilled in the art.

The liquid biopesticide composition may be a liquid or a paste. Such liquid biopesticide compositions may also be characterized in accordance with certain physical properties, e.g., viscosity. Accordingly, certain implementations of a liquid biopesticide composition may have a viscosity in excess of about 0.3 cP. Frequently, the liquid biopesticide composition may have a viscosity from about 0.75 cP to about 1.5 cP and the paste version will have a viscosity in excess of about 25 cP. The resultant liquid biopesticide composition may be applied en masse to a target environment using a variety of techniques known in the art, e.g., ultra-low volume (ULV) spray, high volume (HV) spray, as well as other spray and spreading techniques developed to meet the required volume of application in light of the viscosity of the biopesticide composition.

Regardless of whether the biopesticide composition in accordance with concepts of the present invention is one of the various solid or liquid configurations discussed above, it is contemplated that the composition may include additives that can modify its configuration, facilitate spore growth, or generally increase mortality of the targeted pest. One additive may improve adhesion of a biopesticide composition to a target surface, e.g., a leaf. A sticker, e.g., ADDIT, is a suitable additive that can be used with the liquid biopesticide composition in a manner that causes droplets resulting from application of the liquid biopesticide composition to adhere to a leaf. Another additive, e.g., INDUCE, SILWET or COHERE (nonionic and anionic surfactants and stickers), may alter surface tension of the biopesticide composition in a manner that causes a liquid biopesticide to form substantially uniform droplets, films, and/or layers on a target surface, as desired.

Each of the resultant granules, droplets, films, and layers formed from a biopesticide composition in accordance with concepts of the present invention may include a combination of a sweet whey product, spores, a carrier, and/or other additives (e.g., humectants, antimicrobials, stickers, etc.) so as to form individualized growing environments that may promote spore growth. As discussed with reference to the figure below, each growing environment, or micro-factory, is contemplated to include all of the components necessary for self-sufficient reproduction of spores so as to substantially increase individual spore concentration in most environments, from a pre-application concentration to a post-application concentration, by at least a multiple of ten (10) after fourteen (14) days of environmental conditions suitable for growth, i.e., sufficient temperature and moisture. However, it is understood that certain characteristics of individual biopesticide life history parameters may conspicuously extend the period in which said 10× production is achieved. This increase in spore concentration will improve the chances that targeted pests will contact sufficient spores, which will result in increased mortality at much lower pre-application concentrations than would otherwise be required.

Generally, pest management practices using the biopesticide compositions described above may require a targeted approach that is developed as part of an overall management strategy. Once an infective species is identified, for instance, an effective fungal spore, conidia, mycelium, or other fungal unit from a pathogenic fungi can be identified based on scientific research, laboratory experiments, or other investigative procedures known in the art. A biopesticide suspension may be prepared using the selected fungal unit, an amount of a sweet whey product found to be effective at growing the identified fungal spores, a carrier suitable for the targeted environment, and one or more of the additives described in detail above. The resultant suspension may then be applied to a targeted region and allowed to incubate under the ambient environmental conditions for a period of time, as desired.

It is also contemplated that part of the management strategy may further include additional evaluation and experimentation that follow the incubation period. Test samples, for instance, may be gathered for analysis to understand the efficacy of the initial biopesticide suspension based on the final concentration of the fungal spores, mortality levels of the targeted pests, or other evaluation metrics recognized and/or developed in the art. Evaluation of these metrics may lead to changes in the biopesticide composition, such as, for example, adjustments in the amount of the sweet whey product, or changes in one more of the other additives. For instance, it may be found that the biopesticide composition as formulated does not adhere to the surfaces in the targeted region in a manner that provides effective contact with the targeted pest. The resulting adjustment to the biopesticide might include changing the sticker, discussed above, or adjusting its concentration, so as to promote better adhesion of the biopesticide composition after it is applied to the targeted environment.

EXPERIMENTAL EXAMPLES

Referring now to the drawings, FIG. 1 is a graph that compares the final spore concentration for micro-factories formed from different liquid biopesticide compositions in accordance with concepts of the present invention. As can be seen, each biopesticide composition includes a different respective percentage of the same sweet whey product. Table 2 below summarizes each sample by, respectively, indicating the amount of sweet whey product and the amount of carrier (i.e., sterilized distilled water) that were combined and then were further diluted to achieve the final respective percentage composition of sweet whey product that were:

TABLE 2

| Initial Biopesticide Compositions | | |
|---|---|---|
| | Sweet Whey (g) | Carrier (g) |
| 0% | 0 | 22.5 |
| 5% | 1.25 | 22.5 |
| 10% | 2.5 | 22.5 |
| 15% | 3.75 | 22.5 |

Test samples were prepared by mixing a 4.5 ml sample of each biopesticide composition above with a 0.5 ml sample of a mycopathogenic fungi, i.e., *Lecanicillium muscarium* (an insect-killing fungus that is registered and commercially available in the European Union), to form a 5 ml sample of each respective biopesticide composition with an initial spore concentration of, respectively, about $1\times10^6$, about $1\times10^7$ and about $1\times10^8$ (spore/ml) and the percentage of sweet indicated. Each of the biopesticide compositions were sprayed onto a dry Petri-dish (60×15 mm) and held in a humidified environment to form micro-factories intended to produce spores. The combination of a sweet whey product and spores results in spore production for each of the sweet whey fungal compositions when compared to the control (0%).

Example I

A biopesticide composition having a low concentration of sweet whey (5%) was examined to evaluate the amount of spore growth. As can be seen in FIG. 1, the comparison of the spore growth in each of the initial concentrations for sweet whey (5%) exceeds the spore growth when no sweet whey is used (0%). Examining the results, it is noted that sweet whey (5%) generates at least a 25-fold increase in spore concentration after seven (7) days when an initial spore concentration $1\times10^6$ is used, for example, when compared to the control without sweet whey (0%) after seven (7) days. The $1\times10^7$ spore produced a first multiple of spores equivalent to a 16-fold increase when compared to the control without sweet whey (0%) after seven (7) days. These increases in spore growth are notable because they permit use of a biopesticide composition that is less expensive due to the lower concentration yet, after a relatively brief time in the targeted region achieves a spore concentration that is high enough that a desired pest mortality rate can be achieved.

Example II

A biopesticide composition having a moderate concentration of sweet whey (10%) was also examined to evaluate the amount of spore growth. Here, it can also be seen that spore growth in each of the initial concentrations for sweet whey (10%) exceeds the spore growth when no sweet whey is used (0%) and also when a low concentration of sweet whey is used (5%). From the results, it is noted that sweet whey (10%) generates at least a 5-fold increase in spore concentration after seven (7) days. The $1\times10^6$ initial spore concentration, for example, produced a first multiple of spores equivalent to a 42-fold increase when compared to the control without sweet whey (0%) after seven (7) days. The $1\times10^7$ produced a first multiple of spores equivalent to a 29-fold increase when compared to the control without sweet whey (0%) after seven (7) days. These increases in spore growth are notable because they permit use of a biopesticide composition that is less expensive due to the lower concentration yet, after a relatively brief time in the targeted region achieves a spore concentration that is high enough that a desired pest mortality rate can be achieved.

Example III

A biopesticide composition having a high sweet whey concentration (15%) was also examined for the amount of spore growth. Again, it can be observed that spore growth in each of the initial concentrations for sweet whey (15%) exceeds the spore growth when no sweet whey is used (0%), when low concentrations of sweet whey is used (5%), and also when moderate concentrations of sweet whey is used (10%). The results indicate that sweet whey (15%) provides a growing environment that generates at least a 6-fold increase in spore concentration after seven (7) days. The $1\times10^6$ initial spore concentration, for example, produced a first multiple of spores equivalent to a 77-fold increase when compared to the control without sweet whey (0%) after seven (7) days. The $1\times10^7$ produced a first multiple of spores equivalent to a 41-fold increase when compared to the control without sweet whey (0%) after seven (7) days. These increases in spore growth are notable because they permit use of a biopesticide composition that is less expensive due to the lower concentration yet, after a relatively brief time in the targeted region achieves a spore concentration that is high enough that a desired pest mortality rate can be achieved.

As described in connection with Examples I, II, and III above, it is also noted that all of the sweet whey concentrations (i.e., 5%, 10%, and 15%) produced generally similar first multiples of spores for, respectively, the $1\times10^6$ and $1\times10^7$ initial concentrations. Such a similarity indicates that certain implementations of the biopesticide composition may facilitate spore production while using a lower initial concentration of spores. This lower concentration could provide substantial savings when the initial composition is formulated, thereby reducing overhead and improving the economic viability of the biopesticide composition in accordance with concepts of the present disclosure. Moreover, it is further contemplated that the micro-factories, formed using a sweet whey fungal composition and placed under optimal environmental conditions, provide a growth environment that measurably increases the number of spores that may be observed in as few as about four days. The measurable increase improves to at least about ten-fold after about seven (7) days in most environments. Slower growth may occur when certain embodiments of the biopesticide composition are applied under unfavorable environment conditions of the target region, e.g. a temperature below 68° F., in which case at least about a ten-fold increase in spores will be achieved in no more than thirty (30) days, again dependent on specifics of life histories of individual biopesticide entities as mentioned earlier.

Figure 2:
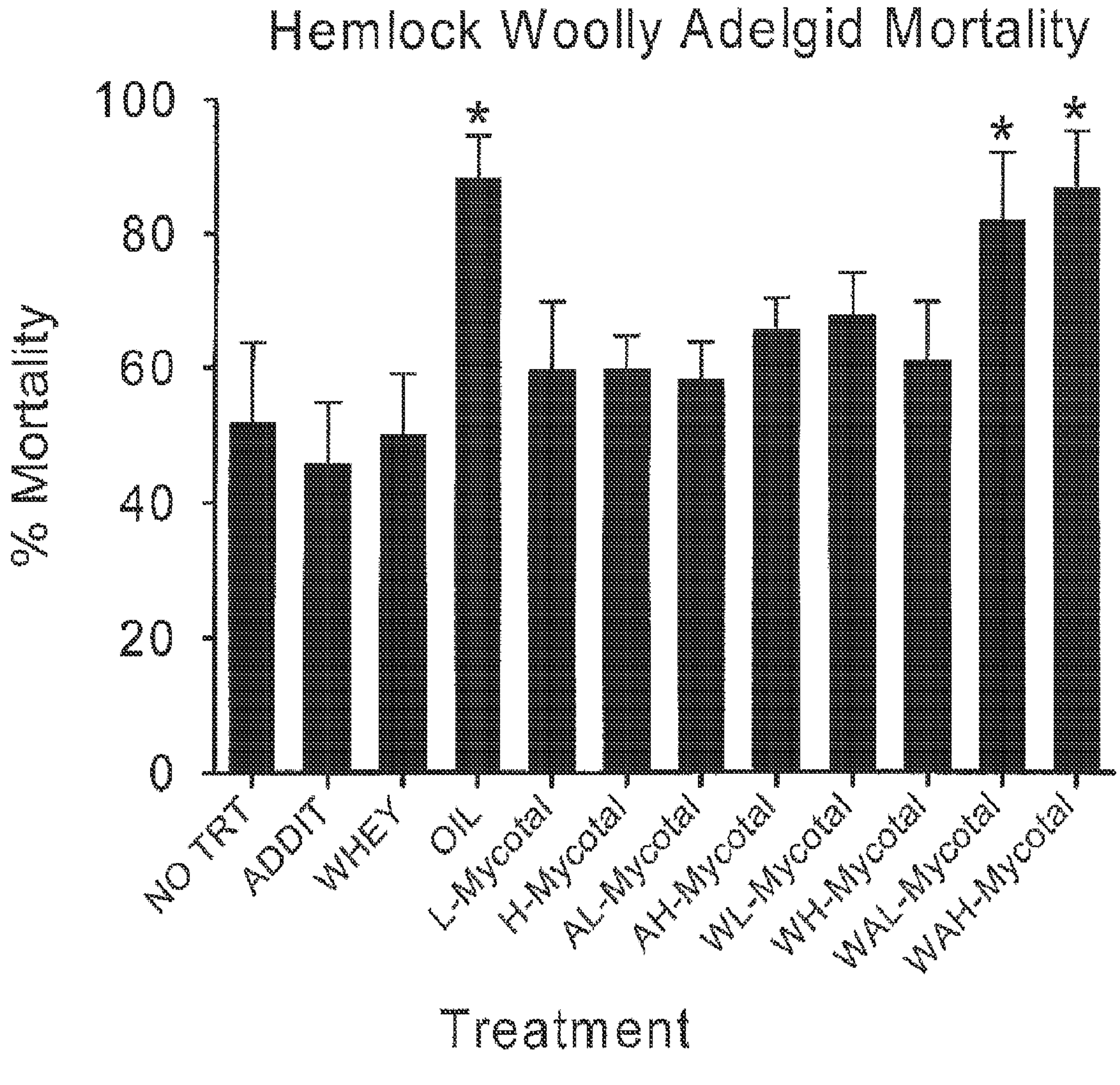
FIG. 2 is a graph that compares the mortalities of a target insect treated with several biopesticide compositions.
Figure 3:
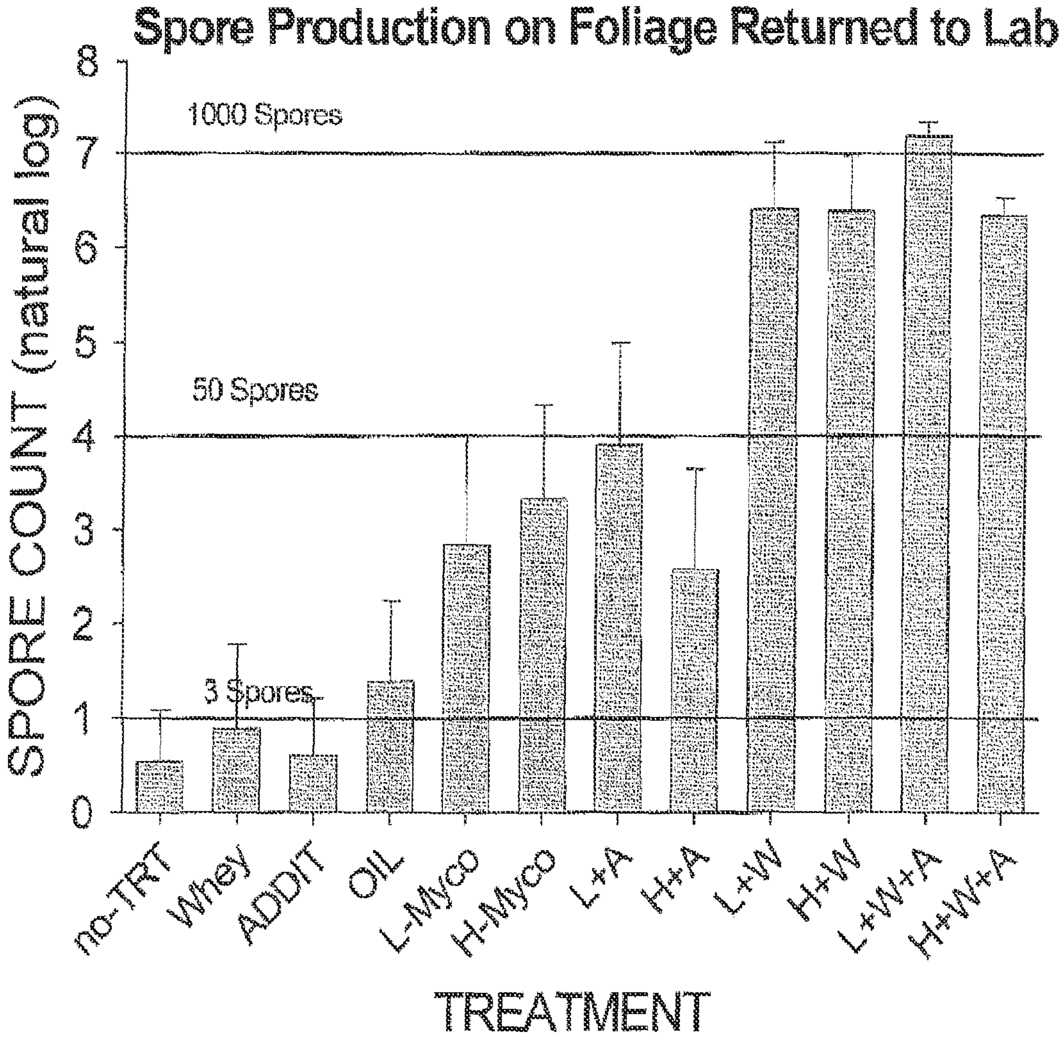
FIG. 3 is a graph that compares the final spore concentration for micro-factories formed from several biopesticide compositions.

Referring back to the drawings, FIGS. 2 and 3 are, respectively, a graph that compares the mortality of hemlock woolly adelgid larvae and a graph that compares the final spore concentration for micro-factories. Each graph in FIGS. 2 and 3 shows results for different liquid compositions in accordance with concepts of the present invention. As will be discussed in more detail below, it will be recognized by those ordinarily skilled in the art that the different liquid compositions include both (i) control samples that do not include fungal material and (ii) biopesticide compositions in accordance with concepts of the present invention. Each of the liquid test compositions were prepared by combining one or more of the following components with a carrier, i.e., sterilized distilled water: (a) spores from the mycopathogenic fungi *Lecanicillium muscarium* (i.e., Mycotal provided by Koppert Biological Systems of The Netherlands); (b) a sweet whey product; and/or (c) one or more additives (i.e., oil, ADDIT, carboxyl methyl cellulose (CMC)).

The control test samples included, an untreated hemlock branch (NO TRT), and water and an appropriate amount of additives to form the following test samples with the corresponding weight percentages: (i) water and ADDIT (0.25%) (ADDIT); (ii) water, sweet whey product (5%), and CMC (0.1%) (WHEY); (iii) water and oil (1%) (OIL). The biopesticide compositions, on the other hand, included water, spores, and/or one or more of the components to form the following test samples with the corresponding weight percentages: (iv) water and Mycotal (0.2 g/l) with a spore concentration of $2\times10^6$ (L-MYCOTAL); (v) water and Mycotal (1 g/l) with a spore concentration of $1\times10^7$ (H-MYCOTAL); (vi) water, ADDIT (0.25%), and Mycotal (0.2 g/l) with a spore concentration of $2\times10^6$ (AL-MYCOTAL); (vii) water, ADDIT (0.25%), and Mycotal (1 g/l) with a spore concentration of $1\times10^7$ (AH-MYCOTAL); (viii) water, sweet whey product (5%), CMC (0.1%), and Mycotal (0.2 g/l) with a spore concentration of $2\times10^6$ (WL-MYCOTAL); (ix) water, sweet whey product (5%), CMC (0.1%), and Mycotal (1 g/l) with a spore concentration of $1\times10^7$ (SH-MYCOTAL); (x) water, sweet whey product (5%), CMC (0.1%), ADDIT (0.25%), and Mycotal (0.2 g/l) with a spore concentration of $2\times10^6$ (SAL-MYCOTAL); and (xii) water, sweet whey product (5%), CMC (0.1%), ADDIT (0.25%), and Mycotal (1 g/l) with a spore concentration of $1\times10^7$ (SAH-MYCOTAL).

Field efficacy data to determine the effective mortality of each test sample composition was determined by implementing a specific test protocol on sixty hemlock branches. The test protocol called for approximately 200 ml of each test sample to be randomly applied with a hand-held sprayer to five (5) 1-meter long hemlock branches infested with aestivating hemlock woolly adelgid. The treated hemlock branches were left to incubate at ambient environmental conditions for about 9 weeks. After the incubation period, Adelgid mortality was assessed by examining five (5) twigs/branch in the field.

Spore growth data to determine the effective spore production of each test sample composition was determined by implementing an additional test protocol as part of the protocol described in connection with insect mortality above. In this case, sub-samples of the treated hemlock branches were immediately removed from the forest to a laboratory environment and held in sealed Petri dish plates lined with filter paper moistened with water to elevate humidity for an incubation period of thirteen (13) days. After the incubation period, spore production was assessed by counting the number of spores on each treated hemlock branch using an adhesive tape method that removes spores from the foliage for microscopic enumeration in accordance with methods familiar to those ordinarily skilled in the art.

Example IV

As can be seen in FIG. 2, the comparison of mortality in each of the test sample compositions with sweet whey (5%) and Mycotal substantially meets or exceeds the mortality when no sweet whey is used (i.e., NO TRT, ADDIT, WHEY). Test compositions with Mycotal augmented with ADDIT exhibit similar results. It is noted that although the 1% horticultural oil (OIL) test sample exceeds the mortality of all other treatments, the OIL treatment is generally recognized in the art as inconsistent with biological pest management and biopesticide compositions in accordance with the present invention. The OIL sample, however, is included as a positive control treatment.

Examining the results, it is noted that the level of mortality in the biopesticide compositions that include sweet whey (5%), ADDIT, and Mycotal (i.e., WAL-Mycotal, WAH-Mycotal) is similar to the level of mortality achieved with the OIL treatment discussed above. Further, while each of the Mycotal test compositions showed increased mortality when compared to the control (i.e., NO TRT), it is noted that biopesticide compostions WAL-Mycotal and WAH-Mycotal show substantially better mortality ($P\leq0.05$) than biopesticide compositions that include sweet whey (5%) but do not include ADDIT or, alternatively, that include ADDIT but do no include sweet whey (5%). Such an increase in mortality is notable because it indicates the positive effect of ADDIT in connection with a biopesticide composition in accordance with concepts of the present invention (i.e., a biopesticide composition that includes a sweet whey product). This increase in mortality also indicates that a biopesticide composition that includes sweet whey (5%) and ADDIT may permit the corresponding biopesticide composition to include a lower concentration of spores than a biopesticide composition that includes only spores.

Example V

A biopesticide composition containing sweet whey (5%), augmented with CMC and containing ADDIT and having either low or high concentration of biopesticide produced significant increases in hemlock woolly adelgid mortality as compared to untreated controls or treatments without the sweet whey and or ADDIT. As can be seen in FIG. 2, the comparison of mortality with the biopesticide treatment augmented with sweet whey and ADDIT significantly ($P\leq0.05$) exceeds the mortality when no sweet whey is used. Examining the results, it is noted that the mortality of the insect when the combination of sweet whey and ADDIT is used exceeds that of when either of these are tested with the biopesticide or alone indicating the positive effect of incorporating the adjuvant ADDIT. The increases in mortality are notable because they permit use of a lower level of biopesticide not able to produce mortality in and of itself.

As discussed above in connection with FIG. 3, foliage returned to the lab and held at elevated humidity produced significantly elevated levels of additional spores over that applied. The experimental treatment were the same as for FIG. 2 and foliage was removed from identical trees. Microfactory production of *L. muscarium* spores was evaluated after thirteen (13) days on foliage returned immediately to the lab post-treatment and held. Foliage was held in sealed Petri dish plates lined with filter paper moistened with water. Counts of spore were made using an adhesive tape method that remove spores from foliage for microscopic enumeration using methods familiar to those skilled in the art.

Example VI

As can be seen in FIG. 3, the comparison of the spore production in each of the test sample compositions that includes sweet whey (5%), i.e., L+W (i.e., L-Mycotal and sweet whey (5%)), H+W (i.e., H-Mycotal and sweet whey (5%)), L+W+A (i.e., L-Mycotal, sweet whey (5%) and ADDIT), and H+W+A (i.e., H-Mycotal, sweet whey (5%) and ADDIT), exceeds the spore production when no sweet whey is present in the sample, i.e., L-Myco, H-Myco, L+A (i.e., L-Mycotal and ADDIT), and L+H (i.e., L-Mycotal and ADDIT). Examining the results, it is noted that sweet whey (5%) and an initial concentration of spores ($2\times10^6$) (L+W) generates at least about a 21-fold increase in spore concentration after thirteen (13) days when compared to a test composition when no sweet whey is used (0%) (L-Myco). It is also noted that sweet whey (5%) and an initial concentration of spores ($1\times10^7$) (H+W) generates at least a 27-fold increase in spore concentrations after thirteen (13) days when compared to test composition when no sweet whey is used (0%) (H-Myco). These increases in spore growth are notable because they permit use of a biopesticide composition that is less expensive due to the lower concentration yet, after a relatively brief time in the targeted region achieves a spore concentration that is high enough that a desired pest mortality rate can be achieved.

A biopesticide composition having a low concentration of sweet whey (5%) was examined to evaluate the amount of spore growth. As can be seen in FIG. 3, the comparison of the spore growth in each of the initial concentrations for sweet whey (5%), i.e. LW, HW, LWA and HWA, exceeds the spore growth when no sweet whey is used (0%), i.e. all other treatments. Examining the results, it is noted that sweet whey and low concentration ($2\times10^6$) of spores (LW) generates at least a 21-fold increase in spore concentration after thirteen (13) days when compared to the control without sweet whey (L-Myco) after thirteen (13) days. It is also noted that sweet whey and high concentration ($1\times10^7$) of spores (HW) generates at least a 27-fold increase in spore concentration after thirteen (13) days when compared to the control without sweet whey (H-Myco) after thirteen (13) days. These increases in spore growth are notable because they permit use of a biopesticide composition that is less expensive due to the lower concentration yet, after a relatively brief time in the targeted region achieves a spore concentration that is high enough that a desired pest mortality rate can be achieved.

As described in connection with examples IV, V, and VI, it is also noted that a biopesticide composition that includes sweet whey (5%), ADDIT, and Mycotal in low and high concentrations produced increased number of spores under laboratory condition (FIG. 3). These same biopesticide composition also exhibited significantly higher levels of insect mortality (FIG. 2). It is hypothesized that although the treatments of biopesticide compositions that include sweet whey (5%), but not ADDIT, also produced increased levels of spores under laboratory conditions where high moisture was maintained, the lack of ADDIT affected water moisture balances under natural conditions, which resulted in no increased mortality (FIG. 2).

The experimental results discussed above were gathered from experiments performed in a laboratory under relatively controlled incubating conditions and in a small scale field trial under natural conditions in a hemlock forest. It is hypothesized, however, that a biopesticide composition in accordance with concepts of the present invention that is applied to a larger targeted region, e.g., stands of trees in a forest or agricultural fields, will provide relatively similar increases in the preponderance of spores over a period of time and corresponding increases in target mortality. It is further contemplated that, when adjusted so as to take into consideration the breadth and scope of natural conditions in a manner described above, the biopesticide composition will provided a natural pathogen that effectively manages pests.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A biopesticide composition, comprising:

a plurality of fungal spores; and a liquid sweet whey product nutritive to said plurality of fungal spores and forming at least about 2% by weight percentage of the biopesticide composition, said sweet whey product having a first percentage of lactose of at least about 2% by weight percentage of said liquid sweet whey product.

2. A biopesticide composition according to claim 1, wherein said plurality of fungal spores includes a plurality of pathogenic fungal spores selected from a group consisting of *Lecanicillium muscarium*, *Beauveria bassiana*, and *Entomaphaga maimaiga*, and any combination thereof.

3. A biopesticide composition according to claim 1, wherein said first percentage of lactose ranges from about 2-7% by weight percentage of the biopesticide composition.

4. A biopesticide composition according to claim 1, wherein said composition is a liquid.

5. A biopesticide composition according to claim 1, wherein said composition is a solid.

6. A biopesticide composition according to claim 1, wherein said plurality of fungal spores have a spore concentration ranging from about $1\times10^4$ to about $1\times10^{10}$ spores/ml.

7. A biopesticide composition according to claim 1, wherein said liquid sweet whey product has a titratable acidity ranging from about 0.08 to about 0.32, a pH ranging from about 3 to about 8, and alkalinity of ash ranging from about 112 ml of 0.1 N HCL per 100 grams to about 450 ml of 0.1 N HCL per 100 grams.

8. A biopesticide composition according to claim 1, wherein said liquid sweet whey product has a titratable acidity ranging from about 0.08 to about 0.32.

9. A biopesticide composition according to claim 1, wherein said liquid sweet whey product has a pH ranging from about 3 to about 8.

10. A biopesticide composition according to claim 1, wherein said liquid sweet whey product has alkalinity of ash ranging from about 112 ml of 0.1 N HCL per 100 grams to about 450 ml of 0.1 N HCL per 100 grams.

11. A biopesticide composition according to claim 1, wherein said liquid sweet whey product forms 2-15% by weight percentage of the biopesticide composition.

12. A biopesticide composition applicable to a target region having a plurality of targeted pests, said biopesticide composition comprising:

a fungal material including a plurality of spores selected so as to cause mortality of said plurality of targeted pests; and a drysweet whey product nutritive to said plurality of spores and forming at least about 2% by weight percentage of the biopesticide composition, said dry sweet whey product having a first percentage of lactose of at least about 64% by weight percentage of said dry sweet whey product.

13. A biopesticide composition according to claim 12, wherein said first percentage of lactose ranges from 64% to 78% by weight percentage of said dry sweet whey product.

14. A biopesticide composition according to claim 12 or 13, wherein said liquid sweet whey product has a pH ranging from about 3 to about 8.

15. A biopesticide composition according to claim 12, wherein said dry sweet whey product has a titratable acidity ranging from about 0.08 to about 0.32, a pH ranging from about 3 to about 8, and alkalinity of ash ranging from about 112 ml of 0.1 N HCL per 100 grams to about 450 ml of 0.1 N HCL per 100 grams.

16. A biopesticide composition according to claim 12, wherein said liquid sweet whey product has a titratable acidity ranging from about 0.08 to about 0.32.

17. A biopesticide composition according to claim 12, wherein said liquid sweet whey product has alkalinity of ash ranging from about 112 ml of 0.1 N HCL per 100 grams to about 450 ml of 0.1 N HCL per 100 grams.

18. A biopesticide composition according to claim 12, wherein said composition is a solid that has a plurality of granules.

19. A biopesticide composition according to claim 12, wherein said composition is a liquid with a viscosity ranging from about 0.75 cP to about 1.5 cP.

20. A biopesticide composition according to claim 12, wherein said dry sweet whey product forms 2-15% by weight percentage of the biopesticide composition.

21. A biopesticide composition applicable to a target region having a plurality of targeted pests, said biopesticide composition comprising:

a fungal material including a plurality of spores in a first concentration, said fungal material for causing mortality of a plurality of targeted pests; and a sweet whey product nutritive to said plurality of spores, said sweet whey product being present in a second concentration, said sweet whey product being one of dry form and liquid form, said sweet whey product in dry form having a first percentage of lactose ranging from 64% to 78% by weight percentage of said dry form sweet whey product and said sweet whey product in liquid form having a first percentage of lactose ranging from 2% to 7% by weight percentage of said liquid form sweet whey product;

wherein said first concentration and said second concentration are selected so that said first concentration will increase at least ten times within one week when incubated in a target region having a temperature from about 10° C. to about 30° C. and a relative humidity from about 70% to about 95%.

22. A biopesticide composition according to claim 21, wherein said sweet whey product has a titratable acidity ranging from about 0.08 to about 0.32, a pH ranging from about 3 to about 8, and alkalinity of ash ranging from about 112 ml of 0.1 N HCL per 100 grams to about 450 ml of 0.1 N HCL per 100 grams.

* * * * *